United States Patent [19]

Heikkila et al.

[11] Patent Number: 5,127,957
[45] Date of Patent: Jul. 7, 1992

[54] METHOD FOR THE RECOVERY OF BETAINE FROM MOLASSES

[76] Inventors: Heikki Heikkila, Aallonkohina 4 C 27, SF-02320 Espoo; Goran Hyoky, Raberget D; Jarmo Kuisma, Edis 1 E 38, both of SF-02460 Kantvik, all of Finland

[21] Appl. No.: 622,392

[22] Filed: Nov. 30, 1990

Related U.S. Application Data

[63] Continuation of Ser. No. 311,665, Feb. 15, 1989, abandoned.

[30] Foreign Application Priority Data

Jun. 9, 1988 [FI] Finland ............................ 882740

[51] Int. Cl.$^5$ .......................... C13J 1/06; C13D 3/12; B01D 15/08
[52] U.S. Cl. ...................... 127/47; 127/46.2; 127/46.3; 127/55; 210/656; 210/691; 210/692; 210/673; 210/675
[58] Field of Search ............. 127/46.2, 46.3, 55; 210/656, 673, 675, 691, 692; 260/501.13

[56] References Cited

U.S. PATENT DOCUMENTS

| | | |
|---|---|---|
| 2,985,589 | 5/1961 | Broughton et al. . |
| 3,706,812 | 12/1972 | Derosset et al. . |
| 4,001,112 | 1/1977 | Barker et al. . |
| 4,157,267 | 6/1979 | Odawara et al. . |
| 4,267,054 | 5/1981 | Yoritomi et al. . |
| 4,293,346 | 10/1981 | Landis et al. . |
| 4,312,678 | 1/1982 | Landis ........................ 127/46.2 |
| 4,313,015 | 1/1982 | Broughton . |
| 4,332,623 | 6/1982 | Ando et al. . |
| 4,359,430 | 11/1982 | Heikkila et al. . |
| 4,379,751 | 4/1983 | Yoritomi et al. . |
| 4,402,832 | 9/1983 | Gerhold . |
| 4,404,037 | 9/1983 | Broughton . |
| 4,405,455 | 9/1983 | Ando et al. . |
| 4,412,366 | 11/1983 | Schoenrock et al. . |
| 4,426,232 | 1/1984 | Neuzil et al. . |
| 4,461,649 | 7/1984 | Neuzil et al. . |
| 4,519,845 | 5/1985 | Ou . |
| 4,533,398 | 8/1985 | Neuzil et al. . |
| 4,599,115 | 7/1986 | Ando et al. . |
| 4,970,002 | 11/1990 | Ando et al. ........................ 127/46.2 |

FOREIGN PATENT DOCUMENTS 0279946 12/1987 European Pat. Off. .

OTHER PUBLICATIONS

"A Sequential Chromatographic Process for the Separation of Glucose/Fructose Mixtures", appearing in The Chemical Engineer (Aug./Sep. 1981), pp. 389-393.
Food Engineering, p. 154 (May 1983).

*Primary Examiner*—Theodore Morris
*Assistant Examiner*—P. L. Hailey
*Attorney, Agent, or Firm*—Kenyon & Kenyon

[57] ABSTRACT

A method as provided wherein betaine is separated eluted from beet molasses using a chromatographic simulated moving bed system having at least three chromatographic columns connected in series. The betaine is eluted during the same cycle as sucrose and rest molasses feeding and substantially simultaneous water feeding step, at least one water feeding step, a circulation step, and elution of sucrose, betaine and rest molasses fractions from selected columns.

25 Claims, 3 Drawing Sheets

METHOD FOR THE RECOVERY OF BETAINE FROM MOLASSES

This application is a continuation of application Ser. No. 07/311,655, filed Feb. 15, 1989, now abandoned.

FIELD OF THE INVENTION

The invention relates to a method for the recovery of the valuable substances, particularly betaine and sucrose contained in beet molasses by simulated moving bed chromatography.

BACKGROUND OF THE INVENTION

Betaine is a valuable compound which is used in animal fodders, as well as in pharmaceutical and cosmetic applications.

Betaine occurs in the roots, seed and stems of a great variety of plants. Its concentration in sugar beet is relatively high, 1.0% to 1.5% on a dry solids basis. When sugar beet is processed for the recovery of sucrose, betaine concentrates in the molasses. Beet molasses usually contains from 3% to 8% of betaine calculated on a dry solids basis.

Betaine is an amphoteric compound having the formula:

It is known to recover betaine from beet molasses, rest molasses or vinasse by ion exchange, by crystallization as a hydrochloride, by extraction with an organic solvent, or by chromatography.

A chromatographic method for the recovery of betaine is described in U.S. Pat. No. 4,359,430. This method is a chromatographic process in which molasses which contains betaine, such as beet molasses, is introduced to the top of a column containing a polystyrene sulphonate cation exchange resin in alkali metal form at a flow rate of 0.5 to 2.0 m$^3$/h/m$^2$. Elution with water is carried out for the recovery of betaine, sucrose and rest molasses from the downstream side of the resin bed.

Simulated or pseudo-moving bed chromatography, i.e., a multi-step separation process in which a solution containing two or more substances to be separated is circulated with respect to a stationary phase, has been used for the separation of two components, such as glucose/fructose from high-fructose syrups or sucrose/rest molasses from molasses.

The first commercial simulated moving bed method was described in U.S. Pat. No. 2,985,589. U.S. Pat. No. 4,404,037 describes a simulated moving bed technique wherein carbon is used as an adsorbent for the recovery of sucrose from molasses. U.S. Pat. Nos. 4,426,232 and 4,533,398 describe similar methods wherein zeolite is used as an adsorbent. U.S. Pat. No. 3,997,357 describes a continuous method for the recovery of sucrose from molasses, and U.S. Pat. Nos. 4,519,845, 4,332,623 and 4,405,455 methods for the separation of sucrose from molasses. U.S. Pat. No. 4,461,649 describes a method for simulated countercurrent separation of sugars. A summary of these separation methods is presented in e.g. Food Engineering (Anon) 1983 55 (5) p. 154, and Sugar y Azucar (1987) August, p. 27 and 29 (U. Bhawarda).

Commercial simulated moving bed methods are also described in U.S. Pat. No. 3,732,982, U.S. Pat. No. 4,412,866, and Chemical Engineering 1981 August/September p. 389 to 393 (P. Barker et al.). In EPO application No. 0279 946, a simulated moving bed method is described for the separation of beet molasses into three or more fractions.

However, the recovery of betaine is not disclosed and the performance of the method is low.

Beet molasses contains sucrose, betaine, salts, amino acids and other organic and inorganic components. It is highly desirable to recover betaine in the same cycle as sucrose. However, this has not been possible previously through the use of simulated moving bed methods.

In previous methods for the recovery of betaine from beet molasses using chromatographic methods, the separation capacity and/or the dry content of the separated fractions has been low.

It is therefore an object of the present invention to separate sucrose, betaine, and rest molasses using a chromatographic technique in which all three fractions are recovered during the same cycle.

It is another object of the present invention to recover a betaine-rich fraction by a single fractionation step with no post-fractionation required.

It is another object of the present invention to effect a high performance separation of betaine so that the separation capacity is high, the yield of the different components in the product fractions is high, and the consumption of eluent water is low.

BRIEF DESCRIPTION OF THE DRAWINGS

The following drawings are illustrative of embodiments of the invention and are not meant to limit the scope of the invention as encompassed by the claims.

SUMMARY OF THE INVENTION

In accordance with the above-mentioned objects and others, the following invention provides an improved method for the recovery of betaine and sucrose by a chromatographic simulated moving bed technique comprising separating betaine by elution as a third faction substantially simultaneously with sucrose and rest molasses.

More particularly, the present invention relates to a method for the recovery of betaine and sucrose from beet molasses during the same cycle of a chromatographic simulated moving bed system having at least three chromatographic columns connected in series and adapted for the flow of liquids in a single direction through the columns. The cycle comprises a molasses feeding step comprising feeding a molasses feed solution into one of the columns and substantially simultaneously feeding water into another of the columns, a water feeding step comprising feeding water into one of the columns, a circulation step comprising circulating the molasses feed solution and the water through the columns, and an eluting step comprising eluting a sucrose fraction from one of the columns, and eluting a betaine fraction from one of the columns and eluting a rest molasses fraction from one of the columns.

Preferably one or more, and most preferably two or three product fractions selected from the group consisting of sucrose, rest molasses and betaine are eluted from the columns during the molasses feeding step and the water feeding step. The betaine is preferably eluted during said water feeding step from the bottom of a column downstream (i.e., farther in the direction of flow of said system) from the column into which the water is fed.

In another embodiment, betaine or rest molasses is eluted as substantially separate fractions in addition to betaine during the water feeding step.

In another embodiment, the method further comprises a second circulation step wherein rest molasses is eluted between the first and second circulation steps. The column from which the rest molasses is eluted is positioned farther downstream from the column into which the water is fed.

In other embodiments, the sucrose may be eluted from the same column as betaine prior to said elution of said betaine, and the betaine and the rest molasses may be eluted one after the other from the same column.

Preferable cycles include from about 3 to 14 steps, the most preferable being from about 4 to about 8.

It is also preferable that there be provided from about 3 to about 14 chromatographic columns connected in series, and more preferably from about 4 to about 8 chromatographic columns connected in series. A chromatographic column may comprise one column or a plurality of short columns, each having feed distribution and eluent collecting means.

It is also preferable that the liquid flow rate in the columns is from about 0.5 to about 10 $m^3/h/m^2$.

It is further preferred that an elevated temperature of from about 40° C. to about 85° C. is used during eluation. It is also preferable that a strong acid cation exchange in monovalent form is used as the column filling material.

The eluent solution is preferably water because it is the most practical and economically advantageous. However, other eluents known to those skilled in the art may be used instead.

The present invention is also related to a method for the recovery of betaine and sucrose from beet molasses from a chromatographic simulated moving bed system having at least three chromatographic columns connected in series and adapted for the flow of liquids in a single direction through the columns, sequentially comprising (1) feeding a molasses feed solution into one of the columns, substantially simultaneously feeding water into another column downstream from the column which is fed with the feed molasses solution, and substantially simultaneously eluting product fractions selected from the group consisting of a rest molasses fraction, a betaine fraction followed by a rest molasses fraction, a sucrose fraction, and a sucrose fraction followed by a betaine fraction; (2) circulating the molasses feed solution and the water in the direction of flow through the columns; (3) feeding water into one of the columns and eluting rest molasses, betaine, or both from a column downstream; (4) circulating the molasses feed solution and the water in the direction of flow through the columns; (5) repeating steps (2) and (3) about 1–6 times during one cycle; and (6) repeating step (1) about 1–2 times or more during one cycle.

The method may further comprise repeating the cycle continuously after equilibrium has been reached. By "equilibrium", it is meant that the composition of all fractions is constant and the sum of all fractions corresponds to the composition of the feed solution.

DETAILED DESCRIPTION

Figure 1:
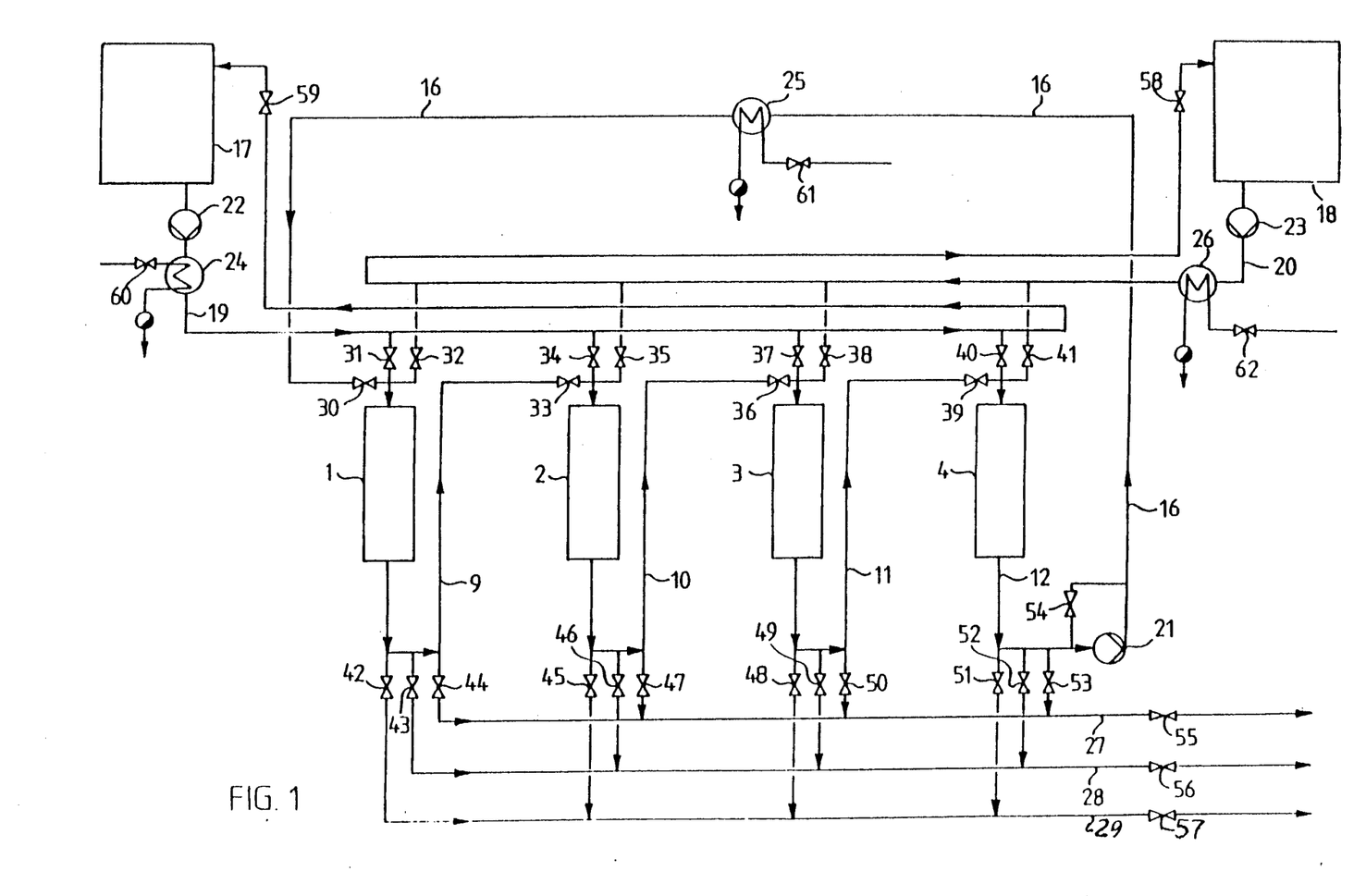
FIG. 1 is a perspective view of an apparatus having four chromatographic columns connected in series.

In the method according to the invention several chromatographic columns are used in series. The series may comprise 3 to 14 columns. The columns are interconnected with pipelines so that the circulation through all the columns can be established with one pump only. In place of one pump, several pumps can be used; for instance, pumps can be provided between several or all columns. The flow rate is 0.5 to 10 $m^3/h/m^2$ of the cross-sectional area of the column. Referring to FIG. 1, an apparatus comprising four chromatographic columns 1–4 connected in series is shown.

The columns are filled with a strong acid, gel-type cation exchange resin (e.g. "Zerolit 225" or "Finex C09" in monovalent ion from), preferably in sodium and/or potassium form.

Figure 2:
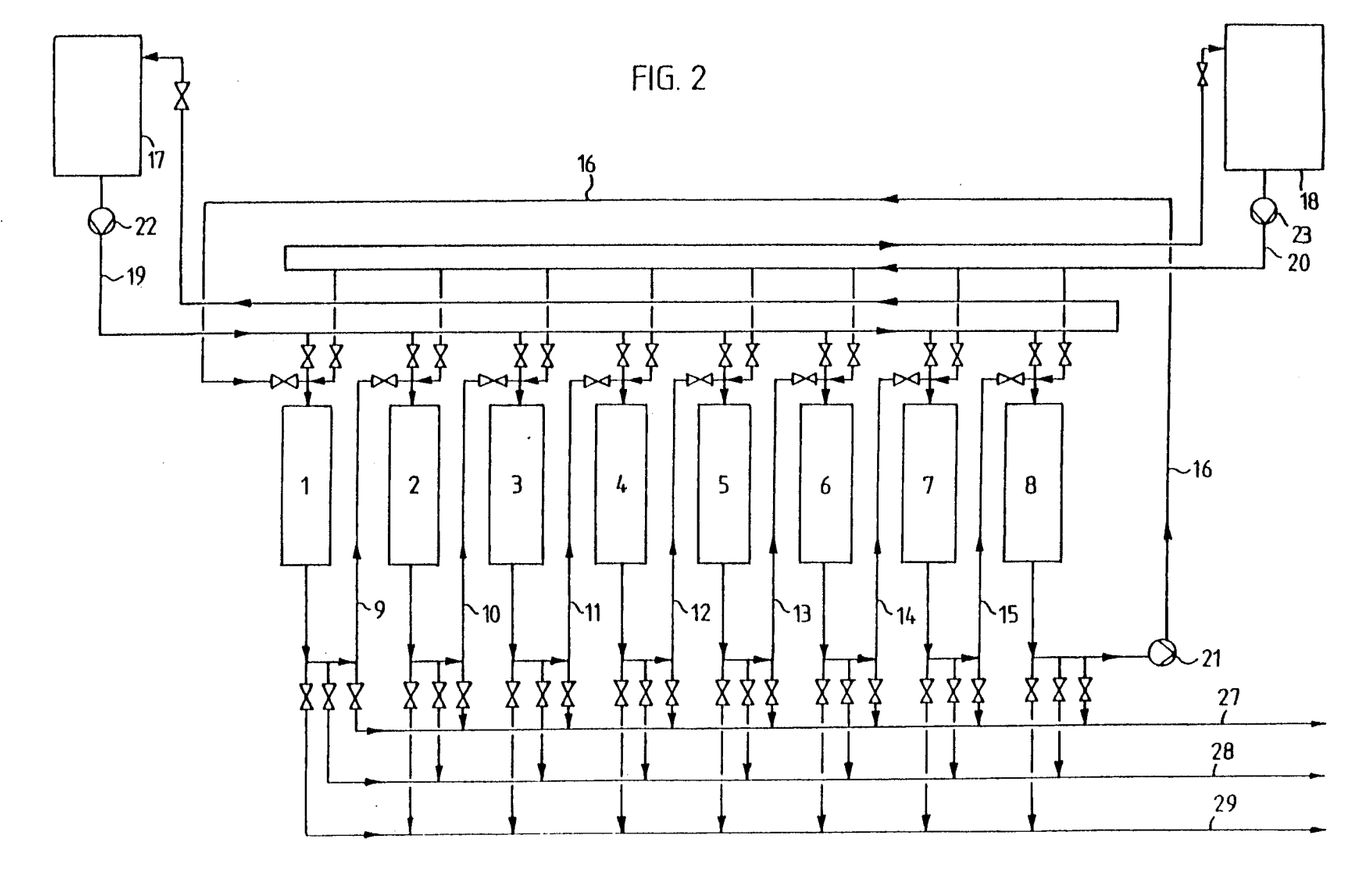
FIG. 2 is a perspective view of an apparatus having eight chromatographic columns connected in series.

FIG. 2 shows another apparatus according to the present invention which is similar to that which is shown in FIG. 1 but in which has eight columns 1–8 connected in series.

The columns are provided with feed lines 19, 20 and product lines 27–29 so that feed solution and eluent water can be fed into the columns and the product fraction collected from the column.

More particularly, a first container 17 is provided which contains diluted molasses fed to a preselected column. The molasses is fed to a preselected column via a molasses feed pump 22 into a molasses feed pipe 19. The apparatus is also provided with a second container 18 which contains water. The water is fed to a preselected column via a water feed pump 23 into a water feed pipe 20. The feed lines 19, 20 and product lines 27–29 as well as the pipelines interconnecting the columns 9–12 are provided with 30–60 valves so that the feeding and the collecting can be interrupted after a preselected amount of the solution has been fed or collected, respectively.

The product lines are provided with on-line instruments (not shown) so that the quality of the product can be monitored during operation. The on-line instruments include a density meter or the like; a refractive index meter, a conductivity meter, a meter for optical activity and a thermometer. The process control is carried out by a microprocessor or computer.

Before undergoing chromatographic separation, the feed solution (beet molasses) is diluted with water to a concentration of from about 40 to 60 percent by weight. The diluted feed solution is, after the addition of sodium carbonate to remove calcium as calcium carbonate, filtered using diatomaceous earth as a filter aid. Before feeding into the separation columns 1–4, the molasses solution is heated by heat exchanger 24 to a temperature ranging from about 50° C. to about 85° C.

Elution is carried out with water which is provided via water container 18, water feed pipe 20, and water feed pump 23. The water is preferably heated in heat exchanger 26 to a temperature of from about 50° C. to about 85° C. before the elution step is carried out.

During the separation, the feed solution batch is circulated through the column series by means of the pump 21. A new portion of feed solution is added to the column series between partly separated rest molasses and sucrose fractions to the top of a preselected column.

For example, when the feed solution is fed into the first column, betaine and rest molasses fractions may be collected from the bottom of the second column. The third column is simultaneously fed with water, and a sucrose fraction can be collected from the fourth column.

It is also possible to elute the sucrose and betaine fractions one after another from the same column by feeding eluent water to the top of a preceding column in the column series. As appears from FIG. 3, sucrose and betaine fractions thereby partly overlap; however, the fractions obtained have sufficient purity.

After the feeding of the feed solution and the eluent water into the columns and the collecting of the product fractions, the circulation of the solutions contained in the columns is started. The circulation of the solutions is continued throughout the entire series of columns until a new batch of feed solution and/or eluent water can be fed again in the same preselected columns as previously used.

If desired, the circulation can be interrupted and water can be fed into the column downstream from the preceding water feeding point for collecting a rest molasses and/or betaine fraction from a column positioned downstream in the column series.

The circulation can be continued until the following feed solution batch or eluent water batch is fed into columns positioned downstream in the column series than during the previous cycle. This improves the efficiency of the separation.

The manner in which it is determined which column is to be eluted in order to obtain betaine, sucrose or rest molasses in accordance with present invention is well known in the art. For example, the elution of sucrose may be determined by on-line optical activity measurement. The elution of ionic non-sugars may be determined by on-line conductivity measurement. The elution of betaine may be determined by the analysis of collected samples. The elution of rest molasses is begun when the density and conductivity measurements begin to increase. These measurements are used to determine the optimum volumes of fractions. In addition, the total dry substance content of a fraction may be determined by an on-line density measurement.

The sucrose content of the sucrose fraction obtained by the method of the present invention may vary from about 80% to about 95% on a dry solids basis, and the betaine content of the betaine fraction from about 25% to about 80% on a dry solids basis. The sucrose content of the rest molasses fraction may vary from about 15% to about 30% on a dry solids basis. These values, however, do not represent actual limits of the performance of the new methods; they are mere examples of a normal operation when using beet molasses containing about 60% of sucrose and about 4.5% to 5.5% of betaine on a dry solids basis.

The dry substance content of the sucrose fraction may vary from 25% to about 35% by weight, and the dry substance content of the betaine fraction and the rest molasses fraction from about 4% to about 10% by weight. These, too, are mere examples of the performances of the new method. The dry content of beet molasses is about 80%.

Betaine may then be recovered from the betaine fraction by any method known in the art. Preferred processes which may be used to recover betaine or pharmaceutical grade betaine monohydrate are set forth in U.S. Pat. No. 4,359,430.

DETAILED DESCRIPTION OF THE PREFERRED EMBODIMENTS

In the following examples the present invention will be illustrated in more detail by describing the separation of beet molasses substantially simultaneously as three fractions using a simulated moving bed technique. These examples should not be considered to restrict the scope of the invention; instead, they are mere examples of the use of the simulated moving bed technique for the recovery of betaine from beet molasses as a third fraction.

EXAMPLE 1

A pilot scale chromatographic equipment was used. A flow sheet is provided in FIG. 2. It comprised eight columns, a feed pump, a circulation pump, an eluent water pump, flow control and pressure control devices, and valves for inlets and outlets of different process streams.

The columns, each of which had a diameter of 200 mm, were filled with a strong acid/cation exchange resin (Finex V09 C09, produced by Finnish Sugar Co. Ltd.). The resin had a polystyrene divinylbenzene matrix and it contained sulphonic acid groups. The resin bed height was 1250 mm in all columns. The average particle size was about 0.36 mm. The resin was initially regenerated into sodium form. During the run, it was gradually equilibrated with the cations contained in the feed molasses. After equilibrium has been achieved, the process can be continued as such for weeks without major changes. The temperature of the solutions introduced into the columns was about 70° C., and the flow rate was 120 liters per hour (1/h).

The feed solution was beet molasses from which calcium had been precipitated by adding sodium carbonate (pH 9). The calcium carbonate precipitate was filtered off.

The separation of sucrose and betaine was carried out by a 5-step sequence where every column had its specific function. The columns were connected in series and the flow direction was always from column no. 1 to column no. 2 etc., and from column no. 8 back to column no. 1, as follows:

Step 1: Molasses was fed into column 1 and rest molasses was eluted from column 6. At the same time water was fed into column 7, and sucrose and betaine, in that order, were eluted from column 8 (see FIG. 3).

Step 2: Water was fed into column 7 and rest molasses was eluted from column 6.

Step 3: Circulation of the solution in all the columns by the circulation pump.

Step 4: Water was fed into column 3 and rest molasses was eluted from column 2.

Step 5: Circulation in all columns.

When the sequence had come to its end, the process control program went on by returning to step 1. By repeating these sequences 5 to 7 times the system was equilibrated and product fractions with constant compositions were eluted and analyzed (see Tables 1 and 2).

The separation was controlled by a microprocessor determining accurately specified volumes of the feed, the circulation and the product fractions.

Figure 3:
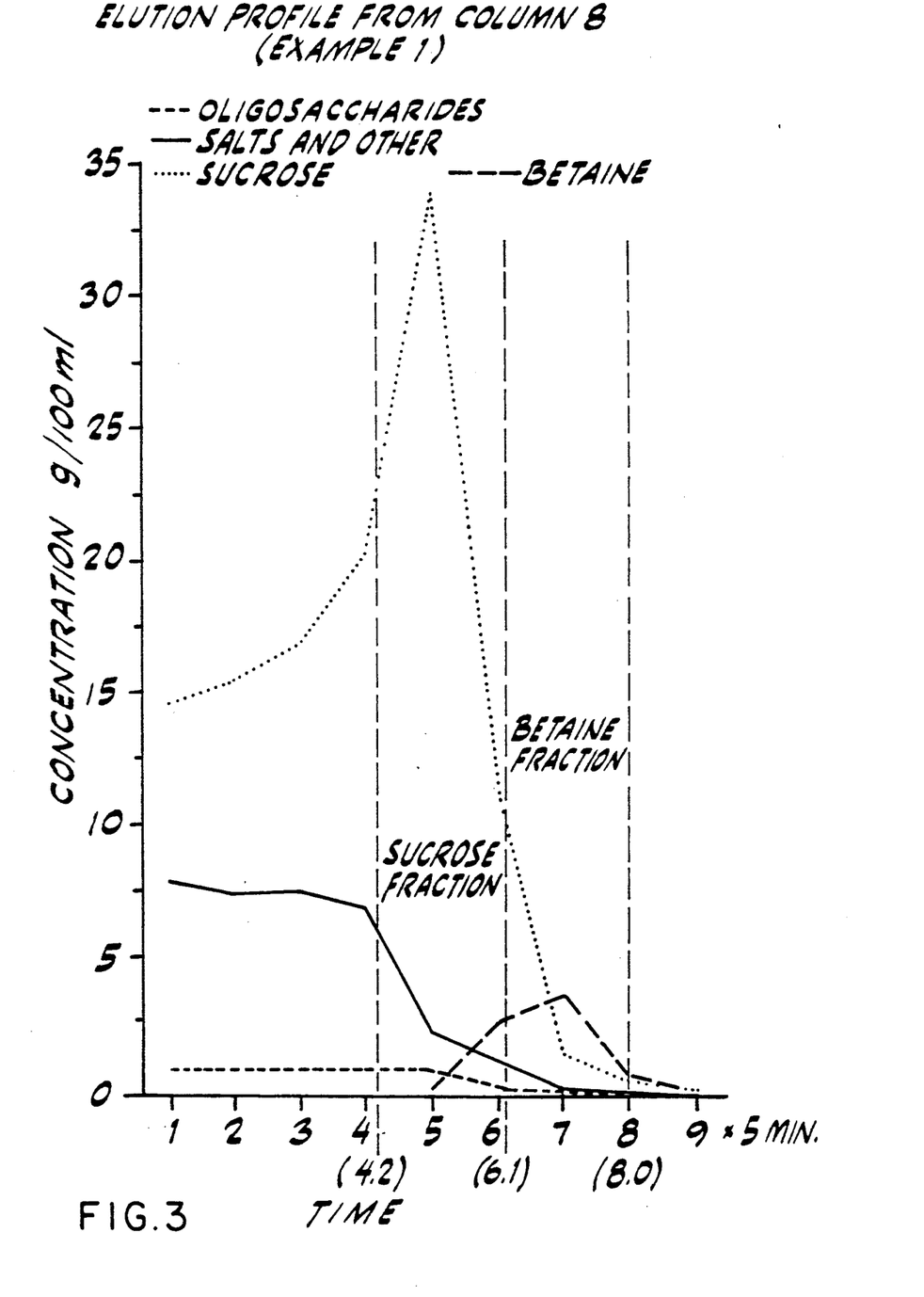
FIG. 3 is a graphical representation of the elution profile from column 8 of Example 1.

Table 1 shows the feed, circulation and product fraction volumes. Table 2 shows the compositions of the feed compositions and the product fractions by weight on a dry solids basis. FIG. 3 is a graphical representation of the elution profile from column no. 1, showing the concentration of salts, oligosaccharides, sucrose and betaine as a function of time.

TABLE 1

Feed, Circulation and Product Fraction Volumes in Liters (l)

| Step No. | 1 | 2 | 3 | 4 | 5 |
|---|---|---|---|---|---|
| Feed | 25 | — | — | — | — |
| Rest molasses fraction | 25 | 15 | — | 30 | — |
| Betaine fraction | 25 | — | — | — | — |
| Sucrose fraction | 25 | — | — | — | — |
| Circulation | — | — | 62 | — | 62 |

TABLE 2

Compositions of the Feed and Product Fractions

| | Dry substance (kg/l) | Sucrose (weight % on d.s.) | Betaine (weight % on d.s.) | Other substances (weight % on d.s.) |
|---|---|---|---|---|
| Feed | 0.623 | 58.4 | 7.6 | 34.0 |
| Rest molasses fraction | 0.104 | 33.3 | 0.6 | 66.1 |
| Betaine fraction | 0.047 | 11.1 | 70.9 | 18.0 |
| Sucrose fraction | 0.295 | 86.8 | 3.3 | 9.9 |

Step 14: Water was fed into column 5 and betaine was eluted from column 4.

Table 3 shows the feed, circulation and product fraction volumes, and Table 4 the compositions of the feed and the product fractions.

TABLE 3

Feed, Circulation and Product Fraction Volumes (l)

| | Volumes (l) | | | | | | |
|---|---|---|---|---|---|---|---|
| Step No. | 1 | 2/9 | 3/10 | 4/11 | 5/12 | 6/13 | 7/14 |
| Feed | 25 | — | — | — | — | — | — |
| Rest Molasses fraction | 25 | — | 25 | — | 10 | — | — |
| Betaine fraction | — | — | — | — | 15 | — | 15 |
| Sucrose fraction | 25 | — | — | — | — | — | — |
| Circulation | — | 70 | — | 56 | — | 56 | — |

TABLE 4

Composition of the Feed and Product Fractions

| | Dry substance (kg/l) | Sucrose (weight % on d.s.) | Betaine (weight % on d.s.) | Other substances (weight % on d.s.) |
|---|---|---|---|---|
| Feed | 0.615 | 58.4 | 7.6 | 34.0 |
| Rest molasses fraction | 0.089 | 23.5 | 4.8 | 71.7 |
| Betaine fraction | 0.082 | 21.9 | 35.9 | 42.5 |
| Sucrose fraction | 0.281 | 92.5 | 0.9 | 6.6 |

EXAMPLE 2

The equipment, the resin and the conditions were the same as in Example 1, except for the flow rate, which was 150 l/h.

The process control was carried out by a 2×7-step sequence. The steps 1 to 7 comprise feeding one batch of molasses and three water eluation steps. The operations in steps 8 and 14 were identical to those in steps 1 to 7, but were performed four columns farther downstream (in the direction of flow the column series):

Step 1: Molasses solution was fed into column 7 and rest molasses was eluted from column 4. At the same time water was fed into column 5 and sucrose eluted from column 6.
Step 2: Circulation in all columns.
Step 3: Water was fed into column 1 and rest molasses was eluted from column 8.
Step 4: Circulation in all columns.
Step 5: Water was fed into column 5 and at the same time betaine and rest molasses, in that order, were eluted from column 4.
Step 6: Circulation in all columns.
Step 7: Water was fed into column 1 and betaine was eluted from column 8.
Step 8: Molasses solution was fed into column 3 and rest molasses was eluted from column 8, and at the same time water was fed into column 1 and sucrose was eluted from column 2.
Step 9: Circulation in all columns.
Step 10: Water was fed into column 5 and rest molasses was eluted from column 4.
Step 11: Circulation in all columns.
Step 12: Water was fed into column 1 and at the same time betaine and rest molasses, in that order, were eluted from column 8.
Step 13: Circulation in all columns.

EXAMPLE 3

The equipment, the resin and the conditions were the same as in Example 2. The process was controlled, as in Example 2, by a 2×7-step sequence. The operations in steps 8 and 14 were identical to those in steps 1 to 7, but they were performed four columns downstream. The main difference was that the betaine fraction was recovered separately from one predetermined column.

Step 1: Molasses was fed into column 1 and rest molasses was eluted from column 4. At the same time, water was fed into column 5 and sucrose eluted from column 6.
Step 2: Circulation in all columns.
Step 3: Water was fed into column 1 and rest molasses was eluted from column 8.
Step 4: Circulation in all columns.
Step 5: Water was fed into column 5 and rest molasses was eluted from column 4.
Step 6: Circulation in all columns.
Step 7: Water was fed into column 1 and betaine was eluted from column 8.
Step 8: Molasses was fed into column 5 and rest molasses was eluted from column 8. At the same time, water was fed into column 1 and sucrose eluted from column 2.
Step 9: Circulation in all columns.
Step 10: Water was fed into column 5 and rest molasses was eluted from column 4.
Step 11: Circulation in all columns.
Step 12: Water was fed into column 1 and rest molasses was eluted from column 8.
Step 13: Circulation in all columns.
Step 14: Water was fed into column 5 and betaine was eluted from column 4.

The fraction volumes appear from Table 5, and the compositions of the feed and product fractions from Table 6.

TABLE 5

Feed, Circulation and Product Fraction Volumes (l)

| Step No. | 1 | 2/9 | 3/10 | 4/11 | 5/12 | 6/13 | 7/14 |
|---|---|---|---|---|---|---|---|
| Feed | 20 | — | — | — | — | — | — |
| Rest molasses fraction | 20 | — | 30 | — | 20 | — | — |
| Betaine fraction | — | — | — | — | — | — | 20 |
| Sucrose fraction | 20 | — | — | — | — | — | — |
| Circulation | — | 56 | — | 55 | — | 55 | — |

TABLE 6

Compositions of the Feed and Product Fractions

| | Dry substance (kg/l) | Sucrose (weight % on d.s.) | Betaine (weight % on d.s.) | Other substances (weight % on d.s.) |
|---|---|---|---|---|
| Feed | 0.615 | 59.0 | 6.1 | 34.9 |
| Rest molasses fraction | 0.058 | 11.3 | 5.4 | 83.3 |
| Betaine fraction | 0.064 | 8.8 | 25.4 | 65.8 |
| Sucrose fraction | 0.358 | 90.1 | 1.4 | 8.5 |

EXAMPLE 4

The equipment, the resin and the conditions were the same as in Examples 1 to 3, except for the number of the columns, which was 4, and the flow rate, which was 120 l/h (the feed, the circulation, and the eluation of rest molasses) and 280 l/h (the eluation of sucrose and betaine). The height of the resin bed was 2500 mm.

The process was controlled by an 8-step sequence.

Step 1: Molasses was fed into column 1 and rest molasses was eluted from column 3. At the same time water was fed into column 4, and sucrose and betaine, in that order, were eluted from the bottom of the same column.

Step 2: Circulation in all columns.

Step 3: Water was fed into column 1 and rest molasses was eluted from column 4.

Step 4: Circulation in all columns.

Step 5: Water fed into column 2 and rest molasses was eluted from column 1.

Step 6: Circulation in all columns.

Step 7: Water fed into column 3 and rest molasses was eluted from column 2.

Step 8: Circulation in all columns.

The feed, circulation and product fraction volumes appear from Table 7 and the compositions of the feed and the product fractions from Table 8.

TABLE 7

Feed, Circulation and Product Fraction Volumes (l)

| Step No. | 1 | 2 | 3 | 4 | 5 | 6 | 7 | 8 |
|---|---|---|---|---|---|---|---|---|
| Feed | 20 | — | — | — | — | — | — | — |
| Rest molasses | 20 | — | 16 | — | 16 | — | 16 | — |
| Betaine | 28 | — | — | — | — | — | — | — |
| Sucrose | 24 | — | — | — | — | — | — | — |
| Circulation | — | 30 | — | 30 | — | 32 | — | 32 |

TABLE 8

Compositions of the Feed and Product Fractions

| | Dry substance (kg/l) | Sucrose (weight % on d.s.) | Betaine (weight % on d.s.) | Other substances (weight % on d.s.) |
|---|---|---|---|---|
| Feed | 0.790 | 62.3 | 6.5 | 31.2 |
| Rest molasses | 0.094 | 30.1 | 2.1 | 67.8 |
| Betaine | 0.045 | 21.1 | 59.1 | 19.7 |
| Sucrose | 0.311 | 89.3 | 1.9 | 8.8 |

Many other variations of the present invention would be obvious to those skilled in the art, and are contemplated to be within the scope of the appended claims. The above-mentioned patents are hereby incorporated by reference.

We claim:

1. A method for the recovery of betaine and sucrose from beet molasses as substantially separate product fractions during the same cycle of a chromatographic simulated moving bed system having at least three chromatographic columns connected in series and adapted for the flow of liquids in a single direction through the columns, said cycle comprising a molasses feeding step comprising feeding a molasses feed solution into one of said columns and substantially simultaneously feeding eluent water into another of said columns, followed by the two following steps either one or several times;

an eluent water feeding step comprising feeding water into one of said columns, and a circulation step comprising circulating said molasses feed solution and said water through said columns, wherein product fractions are eluated during said molasses feeding step, said eluent water feeding step, or both said product fractions selected from the group consisting of a rest molasses fraction, a betaine fraction, and a sucrose fraction, wherein each of said product fractions are recoverable during said cycle.

2. The method of claim 1, wherein said steps are repeated 2 to 6 times during one cycle.

3. The method of claim 1, further comprising eluting rest molasses from one of said columns.

4. The method of claim 1, further comprising eluting a sucrose and a betaine fraction sequentially from one of said columns.

5. The method of claim 1, further comprising repeating said cycle continuously after equilibrium has been reached.

6. The method of claim 1, wherein said molasses feeding step and said water feeding step further comprise eluting two or three product fractions selected from the group consisting of sucrose, rest molasses and betaine from one of said columns.

7. The method of claim 6, wherein said betaine is eluted during said water feeding step from a column downstream from the column into which the water is fed.

8. The method of claim 6, further comprising eluting said rest molasses as a substantially separate fraction in addition to said betaine during said water feeding step.

9. The method of claim 7, further comprising a second circulation step, and eluting a fraction of said rest molasses between said circulation step and said second circulation step, the column from which said rest molasses is eluted being positioned downstream from the column into which the water is fed.

10. The method of claim 9, further comprising eluting said sucrose from the same column as betaine prior to said elution of said betaine.

11. The method of claim 7, further comprising eluting said betaine and said rest molasses one after the other from the same column.

12. The method of claim 8, further comprising repeating said circulation step from about 2 to about 6 times during one cycle.

13. The method of claim 10, further comprising providing from about 3 to about 14 chromatographic columns connected in series.

14. The method of claim 10, further comprising providing from about 4 to about 8 chromatographic columns connected in series.

15. The method of claim 1, wherein a strong acid cation exchange resin is used as an adsorbent in said chromatographic columns.

16. The method of claim 15, wherein said strong acid cation exchange resin is in monovalent form.

17. The method of claim 15, wherein the strong acid cation exchange resin is in sodium form, potassium form, or both.

18. The method of claim 1, wherein the liquid flow rate in said columns is from about 0.5 to about 10 $m^3/h/m^2$.

19. The method of claim 1, wherein the temperature of said circulating feed solution and water is from about 40° C. to about 85° C.

20. A method for the recovery of betaine and sucrose from beet molasses as substantially separate product fractions from a chromatographic simulated moving bed system having at least three chromatographic columns connected in series and adapted for the flow of liquids in a single direction through the columns, sequentially comprising (1) feeding a molasses feed solution into the top of one of said columns and eluting a rest molasses fraction from the bottom of a column downstream from said column top which is fed with said molasses feed solution;

(2) feeding water into one of said columns downstream from said column which is fed with said feed molasses solution at substantially the same time as said feeding of said molasses feed solution, and eluting product fractions comprising a sucrose fraction followed by a betaine fraction from a column downstream from said column which is fed with water;

(3) circulating said molasses feed solution and the water in said direction of flow through said columns without feeding molasses feed solution or water into said column or removing any product fractions;

(4) feeding water into one of said columns and eluting rest molasses from a column downstream from said column which is fed with water;

(5) circulating said molasses feed solution and the water in said direction of flow through said columns;

(6) feeding water into one of said columns and eluting reset molasses from a column downstream from said column which is fed with water; and (7) circulating said molasses feed solution and the water in said direction of flow through said columns.

21. The method of claim 20, further comprising repeating said cycle after equilibrium has been reached.

22. The method of claim 21, further comprising repeating steps 1-8 starring with feeding a molasses feed solution into a column downstream from said column into which said molasses feed solution was fed during the previous cycle.

23. A method for the recovery of betaine and sucrose from beet molasses as substantially separate product fractions from a chromatographic simulated moving bed system having at least three chromatographic columns connected in series and adapted for the flow of liquids in a single direction through the columns, sequentially comprising (1) feeding a molasses feed solution into the top of one of said columns and eluting a rest molasses fraction from the bottom of a column downstream from said column top which is fed with said molasses feed solution;

(2) feeding water into one of said columns downstream from said column which is fed with said feed molasses solution at substantially the same time as said feeding of said molasses feed solution, and eluting a product fraction selected from the group consisting of sucrose, betaine and a sucrose fraction followed by a betaine fraction from a column downstream from said column which is fed with water;

(3) circulating said molasses feed solution and the water in said direction of flow through said columns without feeding molasses feed solution or water into said column or removing any product fractions;

(4) feeding water into one of said columns and eluting rest molasses from a column downstream from said column which is fed with water;

(5) circulating said molasses feed solution and the water in said direction of flow through said columns;

(6) feeding water into one of said columns and eluting betaine molasses from a column downstream from said column which is fed with water; and (7) circulating said molasses feed solution and the water in said direction of flow through said columns.

24. The method of claim 23, further comprising repeating said cycle after equilibrium has been reached.

25. The method of claim 24, further comprising repeating steps 1-8 starting with feeding a molasses feed solution into a column downstream from said column into which said molasses feed solution was fed during the previous cycle.

* * * * *

UNITED STATES PATENT AND TRADEMARK OFFICE
CERTIFICATE OF CORRECTION

PATENT NO. : 5,127,957
DATED : July 7, 1992
INVENTOR(S) : Heikkila, et al It is certified that error appears in the above-identified patent and that said Letters Patent is hereby corrected as shown below:

Abstract, line 6, change "lasses feeding . . ." to --lasses as a third fraction. The method comprises a molasses feeding . . .--.

Column 1, line 6, change "07/311,655" to --07/311,665--.

Column 7, line 42, change "flow" to --flow of--.

Column 10, line 39, change "both" to --both,--.

Column 12, line 5, change "reset" to --rest--.

Column 12, line 13, change "starring" to --starting--.

Column 12, line 50, change "betaine" to --rest--.

Signed and Sealed this

Thirty-first Day of August, 1993

*Attest:*

BRUCE LEHMAN

*Attesting Officer*     *Commissioner of Patents and Trademarks*